(12) United States Patent
Burvall et al.

(10) Patent No.: US 9,072,630 B2
(45) Date of Patent: Jul. 7, 2015

(54) METHOD OF APPLYING STRUCTURAL ELEMENTS TO AN ABSORBENT ARTICLE

(75) Inventors: Angelica Burvall, Bollebygd (SE); Solgun Drevik, Mölnlycke (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/349,639

(22) PCT Filed: Oct. 5, 2011

(86) PCT No.: PCT/SE2011/051192
§ 371 (c)(1),
(2), (4) Date: Apr. 3, 2014

(87) PCT Pub. No.: WO2013/051971
PCT Pub. Date: Apr. 11, 2013

(65) Prior Publication Data
US 2014/0228796 A1    Aug. 14, 2014

(51) Int. Cl.
*A61F 13/15* (2006.01)
*B44C 1/17* (2006.01)
(Continued)

(52) U.S. Cl.
CPC .......... *A61F 13/475* (2013.01); *A61F 13/4752* (2013.01); *A61F 13/494* (2013.01); *A61F 2013/49493* (2013.01); *A61F 13/15707* (2013.01); *A61F 2013/15715* (2013.01);
(Continued)

(58) Field of Classification Search
CPC ................. A61F 13/475; A61F 13/494; A61F 13/15707; A61F 13/4752; A61F 13/4757; A61F 13/4758; A61F 2013/49493

USPC .......... 604/362, 367, 365, 366, 379, 380, 370, 604/378
See application file for complete search history.

(56) References Cited

U.S. PATENT DOCUMENTS

| 4,336,804 A | 6/1982 | Roeder |
| 4,337,772 A | 7/1982 | Roeder |

(Continued)

FOREIGN PATENT DOCUMENTS

| CN | 102065812 A | 5/2011 |
| EP | 0 229 639 A2 | 7/1987 |

(Continued)

OTHER PUBLICATIONS

International Search Report (PCT/ISA/210) mailed on Jun. 7, 2012, by the Swedish Patent Office as the International Searching Authority for International Application No. PCT/SE2011/051192.
(Continued)

*Primary Examiner* — Jacqueline Stephens
(74) *Attorney, Agent, or Firm* — Buchanan Ingersoll & Rooney PC

(57) ABSTRACT

A method of applying structural elements to an absorbent article is disclosed. The absorbent article includes a top sheet and a back sheet. The expandable ink is applied to the top sheet, and the expandable ink is activated to obtain three-dimensional structural elements on the top sheet. An absorbent article is disclosed and includes a top sheet provided with structural elements. The structural elements consist of expandable ink that has been applied to the top sheet and has been subsequently activated to form three-dimensional structural elements.

17 Claims, 4 Drawing Sheets

(51) Int. Cl.
*B44C 1/165* (2006.01)
*A61F 13/475* (2006.01)
*A61F 13/494* (2006.01)
*A61F 13/511* (2006.01)
*A61F 13/513* (2006.01)
*A61F 13/84* (2006.01)
*D06P 5/00* (2006.01)
*D06P 5/20* (2006.01)

(52) U.S. Cl.
CPC ....... *A61F2013/16* (2013.01); *A61F 13/51104* (2013.01); *A61F 13/51394* (2013.01); *A61F 13/84* (2013.01); *A61F 2013/8497* (2013.01); *D06P 5/00* (2013.01); *D06P 5/2077* (2013.01)

(56) References Cited

U.S. PATENT DOCUMENTS

| | | | |
|---|---|---|---|
| 4,376,440 | A | 3/1983 | Whitehead et al. |
| 4,834,739 | A | 5/1989 | Linker, III et al. |
| 4,850,991 | A | 7/1989 | Nakanishi et al. |
| 4,959,265 | A | 9/1990 | Wood et al. |
| 5,431,643 | A | 7/1995 | Ouellette et al. |
| 5,670,110 | A | 9/1997 | Dirk et al. |
| 5,778,457 | A | 7/1998 | Conway |
| 6,004,308 | A | 12/1999 | Haddock |
| 6,099,516 | A | 8/2000 | Pozniak et al. |
| 2002/0098348 | A1 | 7/2002 | McReynolds et al. |
| 2003/0009144 | A1 | 1/2003 | Tanzer et al. |
| 2006/0070701 | A1 | 4/2006 | Kobayashi et al. |
| 2007/0098953 | A1 | 5/2007 | Stabelfeldt et al. |
| 2007/0184258 | A1 | 8/2007 | Stockhelm |
| 2008/0041751 | A1 | 2/2008 | Catalfamo |
| 2008/0091162 | A1 | 4/2008 | Maldonado et al. |
| 2009/0287173 | A1 | 11/2009 | Sosalla et al. |
| 2009/0312733 | A1 | 12/2009 | Pellen et al. |
| 2010/0011562 | A1 | 1/2010 | Cauley et al. |
| 2012/0016331 | A1 | 1/2012 | Drevik |
| 2012/0157952 | A1* | 6/2012 | Poruthoor et al. ............ 604/372 |
| 2012/0232511 | A1* | 9/2012 | Velazquez et al. ............ 604/372 |

FOREIGN PATENT DOCUMENTS

| | | |
|---|---|---|
| EP | 0 471 385 A1 | 2/1992 |
| EP | 0 623 332 A1 | 11/1994 |
| EP | 1 149 628 A1 | 10/2001 |
| EP | 1 426 120 A2 | 6/2004 |
| FR | 2 366 009 A | 4/1978 |
| GB | 2 303 821 A | 3/1997 |
| JP | H03-241079 A | 10/1991 |
| JP | H04-040948 A | 2/1992 |
| JP | H06-245954 A | 9/1994 |
| JP | H07-505549 A | 6/1995 |
| JP | 2000-210332 A | 8/2000 |
| JP | 2003-070841 A | 3/2003 |
| JP | 2005-046263 A | 2/2005 |
| JP | 2005-270233 A | 10/2005 |
| JP | 2006-043198 A | 2/2006 |
| JP | 2009-512489 A | 3/2009 |
| WO | WO 91/13752 A1 | 9/1991 |
| WO | WO 93/19715 A1 | 10/1993 |
| WO | WO 97/23183 A1 | 7/1997 |
| WO | WO 99/20217 A1 | 4/1999 |
| WO | WO 01/10373 A | 2/2001 |
| WO | WO 02/08067 A2 | 1/2002 |
| WO | WO 03/003962 A1 | 1/2003 |
| WO | 2007/049237 A2 | 5/2007 |
| WO | WO 2007/050253 A1 | 5/2007 |
| WO | WO 2010/101502 A1 | 9/2010 |

OTHER PUBLICATIONS

Notification of Transmittal of the International Preliminary Report on Patentability (PCT/IPEA/416) and International Preliminary Report on Patentability (PCT/IPEA/409) mailed on Jan. 8, 2014, by the Swedish Patent Office as the International Searching Authority for International Application No. PCT/SE2011/051192.

"Expandable microspheres in inks: advances in look and feel", Asia Pacific Coatings Journal; Aug. 2009, pp. 32-33.

Office Action issued on Sep. 3, 2014, by the Chinese Patent Office in corresponding Chinese Patent Application No. 201180073251.7, and an English Translation of the Office Action.

Japanese Notice of Reasons for Rejection dated Feb. 9, 2015 issued in the corresponding Japanese Patent Application No. 2014531760 and English translation (10 pages).

* cited by examiner

METHOD OF APPLYING STRUCTURAL ELEMENTS TO AN ABSORBENT ARTICLE

TECHNICAL FIELD

The present disclosure pertains to a method of applying structural elements to the top sheet of an absorbent article, to an absorbent article comprising such structural elements, and to the use of an expandable ink to provide structural elements to the top sheet on an absorbent article.

BACKGROUND ART

Absorbent articles such as panty liners, sanitary napkins and incontinence pads sometimes include three-dimensional elements on their top surface. Such elements may be obtained by embossing of the top sheet layer of the absorbent article. U.S. 2009/0312733A1 shows an example of an absorbent article having three-dimensional elements on the body-facing surface. Embossing is a reliable method, but is somewhat inflexible when it comes to providing a large variety of different patterns of three-dimensional elements, as a special embossing roll has to be obtained for each specific patterns. Also, it is difficult to obtain very fine three-dimensional dots and lines by means of embossing. There is therefore a need for an improved method of applying three-dimensional elements on the top sheet of absorbent articles.

SUMMARY

The present disclosure relates to an improved method of applying structural elements to an absorbent article having a longitudinal direction and a transverse direction, side edges extending in the longitudinal direction and end edges extending in the transverse direction, said absorbent article comprising a top sheet and a back sheet, in which method expandable ink is applied to the top sheet, and the expandable ink is then activated, whereby three-dimensional structural elements are obtained on the top sheet. By forming structural elements on the top sheet by means of application and activation of expandable ink, a variety of patterns can be achieved. Further, the application and activation of the expandable ink allows forming of very precise patterns, and very fine lines and dots.

The expandable ink may be applied on 1-50%, preferably 1-25%, of the surface area of the top sheet, and is typically activated by subjecting the top sheet to heat, for example by means of infra-red radiation, hot air, microwaves, or by a heated embossing roll, or alternatively by means of UV radiation. The expandable ink typically comprises a polymer, a solvent and a blowing agent or expandable microspheres.

The expandable ink may be applied as one or more liquid barriers along at least a part of the longitudinal side edges, which liquid barriers may be formed of continuous or dotted lines. Further, a cluster of dots of expandable ink may be applied in a central part of the article, forming a raised portion, wherein the ratio between the heights of the dots and the distance between the dots in the cluster is at least 1:1. Also, expandable ink may be applied along at least a part of a transverse side edge of the article. The top sheet of the absorbent article has a first surface facing away from the back sheet, and a second surface facing towards the back sheet, and the expandable ink may be applied to one or both of said first and second surfaces.

The present disclosure also relates to an absorbent article comprising a top sheet provided with structural elements, characterised in that the structural elements consist of expandable ink that has been applied to the top sheet and has subsequently been activated to form three-dimensional structural elements, and to the use of an expandable ink to provide structural elements to a top sheet of an absorbent article. The three-dimensional structural elements of the absorbent article advantageously have a height of 0.1-15 mm, preferably 0.5-5 mm, and 1-50%, preferably 1-25% of the top sheet may be covered with expandable ink.

DETAILED DESCRIPTION

Figure 1:
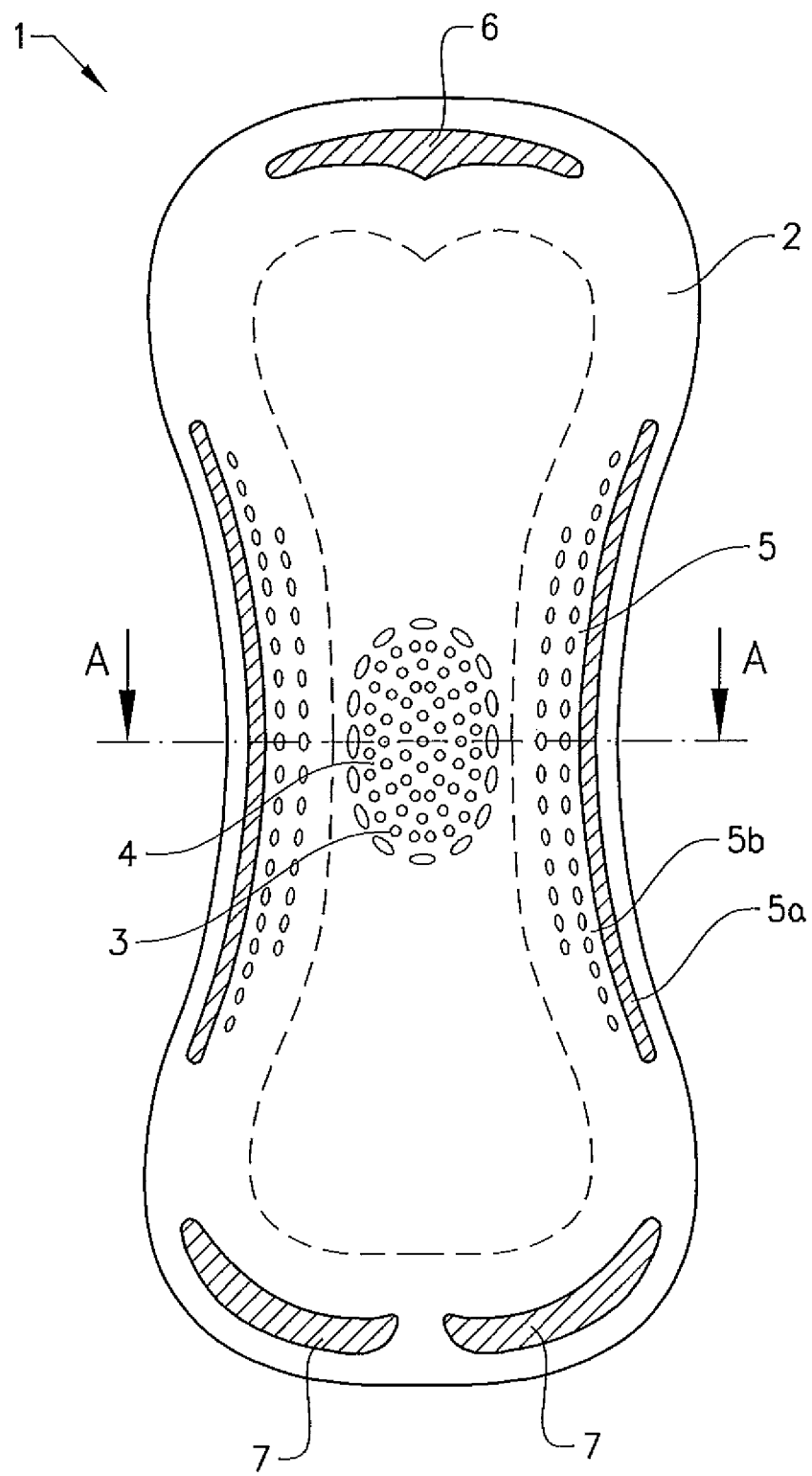
FIG. 1 is a top view of an absorbent pad having three-dimensional structural elements applied to the top sheet.

In the method of the present disclosure structural elements are applied to the top sheet of an absorbent article, comprising a top sheet and a back sheet, and if desired also comprising an absorbent layer arranged between the top sheet and the back sheet. The absorbent article may for example be a sanitary napkin, a panty liner, a male or female incontinence article, a diaper, or any other absorbent article. The expandable ink is expanded so as to be transformed into three-dimensional protruding structural elements as a result of activation. The absorbent article of the present disclosure will be described in more detail below.

The expandable ink used in the method of the present disclosure is preferably non-absorbing, since it is desirable to maintain a dry surface of the top sheet. The ink may also be hydrophilic, in particular when it is desired to obtain improved liquid guiding properties of the top sheet. There may be a mixture of hydrophilic and hydrophobic inks on the same surface of the top sheet or on different surfaces. The hydrophobic ink may be placed on the surface facing the wearer and used as a barrier and a hydrophilic ink may be placed on the surface facing away from the wearer. The expandable ink preferably comprises a polymer, a solvent and a blowing agent or expandable microspheres. The ink may be a standard formulation known to the skilled man in the art, comprising a polymer, a solvent, binders, thickeners, pigments and a blowing agent or expandable microspheres comprising a propellant. The ink may be applied by printing, e.g. by screen printing, flexoprint, ink jet printing, rotary screen printing or gravure.

Application by flexoprint is an advantageous printing method, due to its stability, and insensitivity to dust or particles in the ink. It may also be preferable to combine inks of different colours, in particular when the expandable ink is applied in a pattern for masking absorbed contents of the absorbent article. It may also be preferable to combine inks having different hydrophilicity, density, activating temperatures etc.

The amount of expandable ink applied to the top sheet of the absorbent article will depend on the composition of the ink, on the desired pattern and/or on the desired height of the structural elements after activation of the ink. The amount of ink needed may vary also depending on the surface absorbency. The skilled person can find out the amounts required to achieve the desired surface by routine experiments.

After application of the ink on the absorbent article, any solvents will evaporate so that the ink dries almost instantaneously. As said above, the expandable ink is activated in order to obtain the desired effect. During activation, components of the ink swell up due to the action of blowing agent or microspheres, so that the applied ink is transformed into three-dimensional structural elements, which protrude from the surface of the top sheet of the absorbent article.

The activation may be carried out by exposing the expandable ink to heat, preferably by means of infra-red radiation, hot air, or microwaves. These heating methods allow flexible and versatile heating, which will provide for effective activation of the expandable ink. Alternatively, the ink may be brought into contact with a heated surface, such as an embossing roll. The activation temperature depends on the amount of ink applied and of the type of ink used, and is typically 80 till 180° C., preferably 100-180° C.

If the expandable ink is of a type that can be activated by UV radiation, the activation may instead be performed by means of UV radiation, which may be advantageous in particular when heat-sensitive materials are used in the absorbent article.

The steps of printing and activating can be incorporated as inline steps in a process of manufacturing absorbent articles, or the top sheet can be printed and activated off-line. It is also possible to print the top sheet layer before or during assembly of the components of the absorbent article and to activate the expandable ink in a later stage in the process.

The method of the present disclosure may be performed in an apparatus where equipment for carrying out the steps of application of expandable ink and activation of the ink is arranged such that absorbent article blanks can be fed through each step in a line production, e.g. by arranging discrete absorbent article blanks on a conveyor belt, passing each step of the method. The ink may be applied in different steps. Thus, different types of ink may be applied and activated in different steps.

The expandable ink can be activated so as to obtain expansion only in selected areas, while leaving other areas unexpanded. Thereby, patterns of printed ink can be formed in which some pattern elements are two-dimensional and some pattern elements are three-dimensional. This can be done by masking areas which are not to be activated, or by directing heat or UV radiation only to areas which are to be activated, e.g. by using a directed beam. Hot embossing can also be used for this purpose. By activation the ink in selected areas only, creation of different protruding patterns on the top sheet of absorbent articles can be accomplished, without having to modify the pattern in which the ink is applied.

The expandable ink may be applied in selected areas as desired, and in any desired pattern. The present method allows very accurate patterns of structural elements, and fine lines and dots to be formed on the top sheet. The expandable ink is preferably applied on 1-50% of the surface area of the top sheet, more preferably on 1-25% of the surface area.

When arranged in the absorbent article, the top sheet has a first surface facing away from the back sheet, and a second surface facing towards the back sheet. The expandable ink may be applied to one or both of said first and second surfaces. By applying three-dimensional structural elements on the inside of the top sheet, i.e. on the surface facing towards the back sheet, the volume of the absorbent article can be improved, and the shaping of the article is facilitated, as compared to e.g. cutting the article. By providing structural elements on the outside surface, i.e. the surface facing away from the back sheet, means for directing the liquid flow as desired can be obtained.

As indicated above, the final pattern of structural elements on the top sheet can be obtained by printing the desired pattern of expandable ink or by activating printed expandable ink in a desired pattern, or a combination thereof. Depending on the location and structure of the structural elements applied in this way, various advantageous functional effects can be obtained. Examples of patterns of expandable ink, giving rise to structural elements with different functions are given below. These patterns can be used individually, but can of course advantageously be combined to achieve the desired characteristics of the absorbent article.

For example, the expandable ink may be applied as one or more liquid barriers in the absorbent article, which will minimise the risk of discharged liquid flowing over the edge of the absorbent article. The liquid barriers are formed by applying expandable ink along at least a part of the longitudinal side edges on each side of the absorbent article, for example as continuous or dotted lines. The liquid barriers may preferably have a curved shape, so that the distance between the liquid barrier lines present on each opposing longitudinal side edge is smaller at the centre of the crotch region, and is larger towards the transverse ends of the absorbent article. The curved shape of the barrier lines may approximately follow the outline of the absorbent article in the crotch region. Further, two or more liquid barrier lines having approximately the same curved shape may be arranged adjacent to each other along at least a part of the longitudinal side edges of the article. These liquid barrier lines may be of equal length, or the lengths of the barrier lines may decrease towards the centre of the absorbent article, for obtaining an optimal liquid barrier. When two or more liquid barrier lines are applied on each longitudinal side edge of the absorbent article, they can be all continuous lines or dotted lines, or a combination of continuous and dotted lines can be used. For example, the outermost liquid barrier line may be continuous, and one or more inner liquid barrier lines may be dotted. Barrier lines may also be applied along at least a part of a transverse side edge of the product.

Additionally, clusters of dots of expandable ink may be applied to the top sheet of the absorbent article. The structural elements formed by such dots of expandable ink in a cluster together create a surface having indentations, which act as holes in the surface of the top sheet. Thereby, the flow of liquid over and through the top sheet can be improved and directed in a desired way. This effect can be obtained both when the expandable ink is applied on the first surface facing away from the back sheet, and the second surface facing towards the back sheet.

For example, a cluster of dots of expandable ink forming a raised portion, may be applied in the central part of the top sheet of the article. The ratio between the height of the dots and the distance between the dots in the cluster is at least 1:1, to allow liquid to easily penetrate the top sheet, to maintain good absorption properties of the absorbent article. The dots forming the raised portion may have equal size and height. Preferably, the heights of the dots increase towards the centre of the cluster, to improve body contact with the article, and to improve liquid distribution through the top sheet.

A cluster of dots of expandable ink may also be applied centrally and longitudinally on the top sheet, thus including front, back and the middle part of the absorbent article for masking purposes, where the ratio between the height of the dots and the distance between the dots in the cluster is at least 1:1. The pattern of structural elements in the cluster will obstruct the view of the contents of the absorbent article, such as blood, urine, or faeces. As indicated above it may be desired to combine inks of different colours, to improve masking of the absorbed contents of the absorbent article.

Additionally, the expandable ink may be applied along at least a part of a transverse side edge of the article, so as to form stiffening lines, barrier lines etc. These lines may preferably be continuous lines, and may have a curved shape. At the front transverse side edge of the absorbent article the line may be formed as one structural element, whereas at the rear transverse side edge the lines may be formed as two separate structural elements on each side of a longitudinal centre line of the absorbent article, to improve comfort for the wearer of the absorbent article.

It may also be desirable to apply three-dimensional structural elements as distance elements. For example in diapers and some incontinence articles distance elements can be applied in the rear area of the article, to provide a gap between the surface of the absorbent article and the skin of the wearer.

The present disclosure also pertains to an absorbent article having structural elements which can be obtained by the above described method. The absorbent article may comprise a body facing side of a nonwoven, a film or a laminate thereof and a back sheet of a liquid impervious polymeric film material and an absorbent layer comprising pulp and/or superabsorbent material and/or a fibrous web. The back sheet material may be breathable or non-breathable. The back sheet is facing away from the user during use, and is opposite to the body facing side of the absorbent article. A fastening means may be applied on the back sheet. The structural elements applied on the top sheet of the absorbent article consist of expandable ink that has been applied to the top sheet and that has been subsequently activated to form three-dimensional structural elements, having characteristics as described above. The three-dimensional structural elements preferably have a height of 0.1-15 mm, more preferably 0.5-5 mm. Advantageously, 1-50%, more preferably 1-25% of the surface area of the top sheet is covered with expandable ink which may leave areas of the top sheet uncovered by the expandable ink, thereby allowing a sufficient top sheet free to receive liquid.

The present disclosure also pertains to the use of an expandable ink to provide structural element to a top sheet of an absorbent article. All details and examples described above in relation to the method and the absorbent article apply to this use.

The present disclosure will now be described by way of example, referring to the drawings. The absorbent articles shown in the drawings all have three-dimensional structural elements, having been applied to the top sheet by means of the method of the present disclosure.

Figure 2:
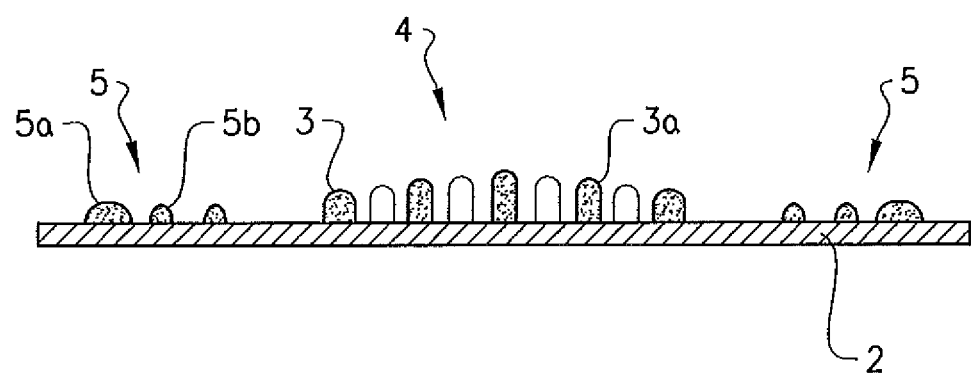
FIG. 2 is a schematic cross-sectional view of the top sheet of the absorbent pad of FIG. 1, along the line A-A in FIG. 1.

FIG. 1 shows an absorbent pad 1 having three-dimensional structural elements of expanded ink applied to the top sheet 2. In the central part of the absorbent pad a cluster of dots 3 are applied, forming a raised portion 4. Liquid barriers 5 are formed along the longitudinal side edges in the crotch region. The liquid barriers comprise a number of curved lines, where the outermost lines 5a are continuous, and the inner lines 5b are dotted. the distance between the liquid barrier lines is smaller at the centre of the crotch region, and larger towards the transverse ends of the absorbent pad. The raised portion 4 can be seen in cross-section in FIG. 2 (taken along the line A-A of FIG. 1), where it is illustrated how the dots 3a in the central portion of the raised portion 4 is higher than the surrounding dots, and the heights of the dots decrease in a direction away from the centre of the raised portion 4. The liquid barriers 5 can be seen at the side edges of the top sheet 2. Stiffening lines 6, 7 are applied at the front and rear transverse ends of the absorbent pad 1. At the rear end, two stiffening lines 7 are applied to improve comfort of the absorbent pad, and at the front end one stiffening line is applied.

Figure 3:
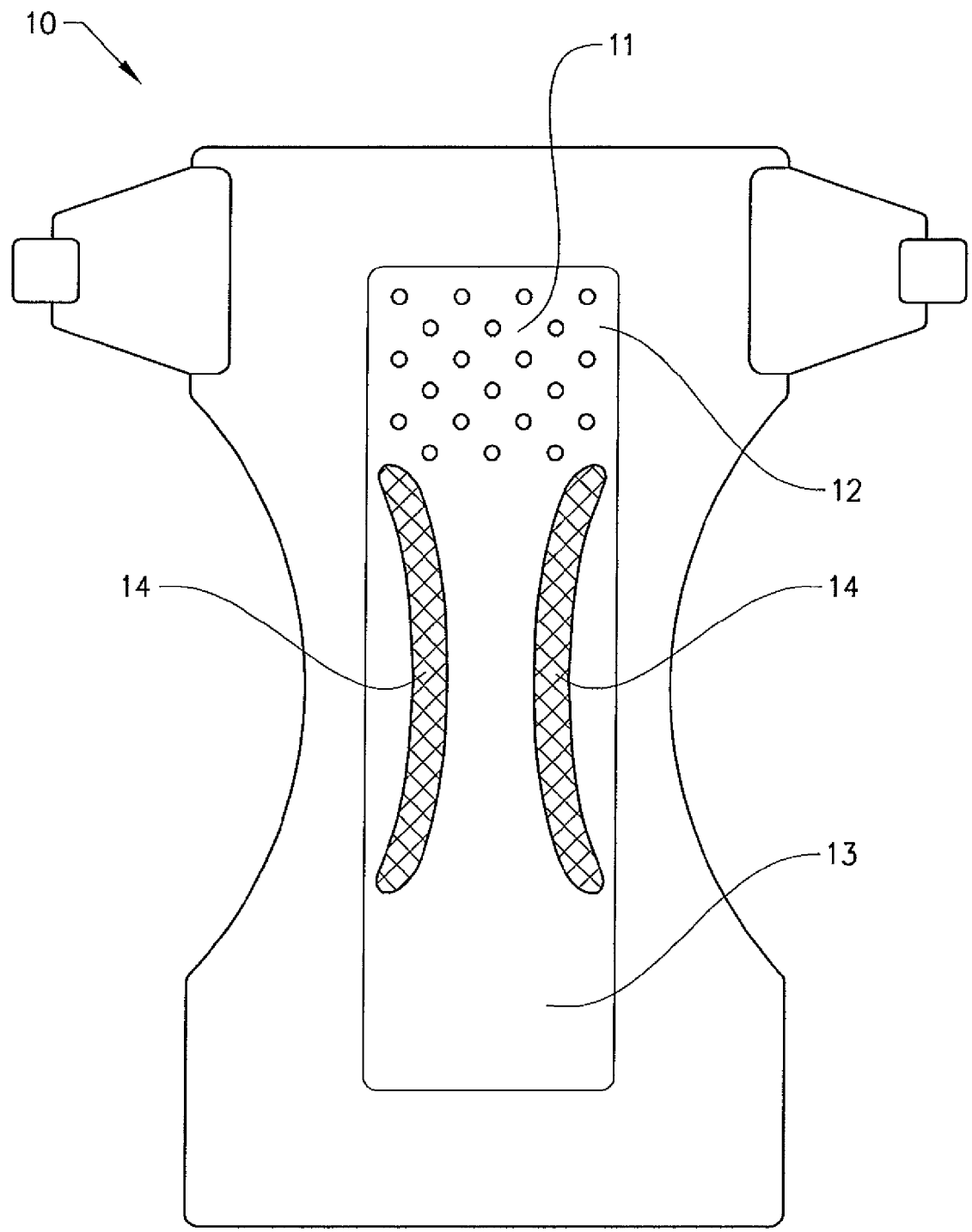
FIG. 3 is a top view of a diaper having three-dimensional structural elements applied to the top sheet.
Figure 4:
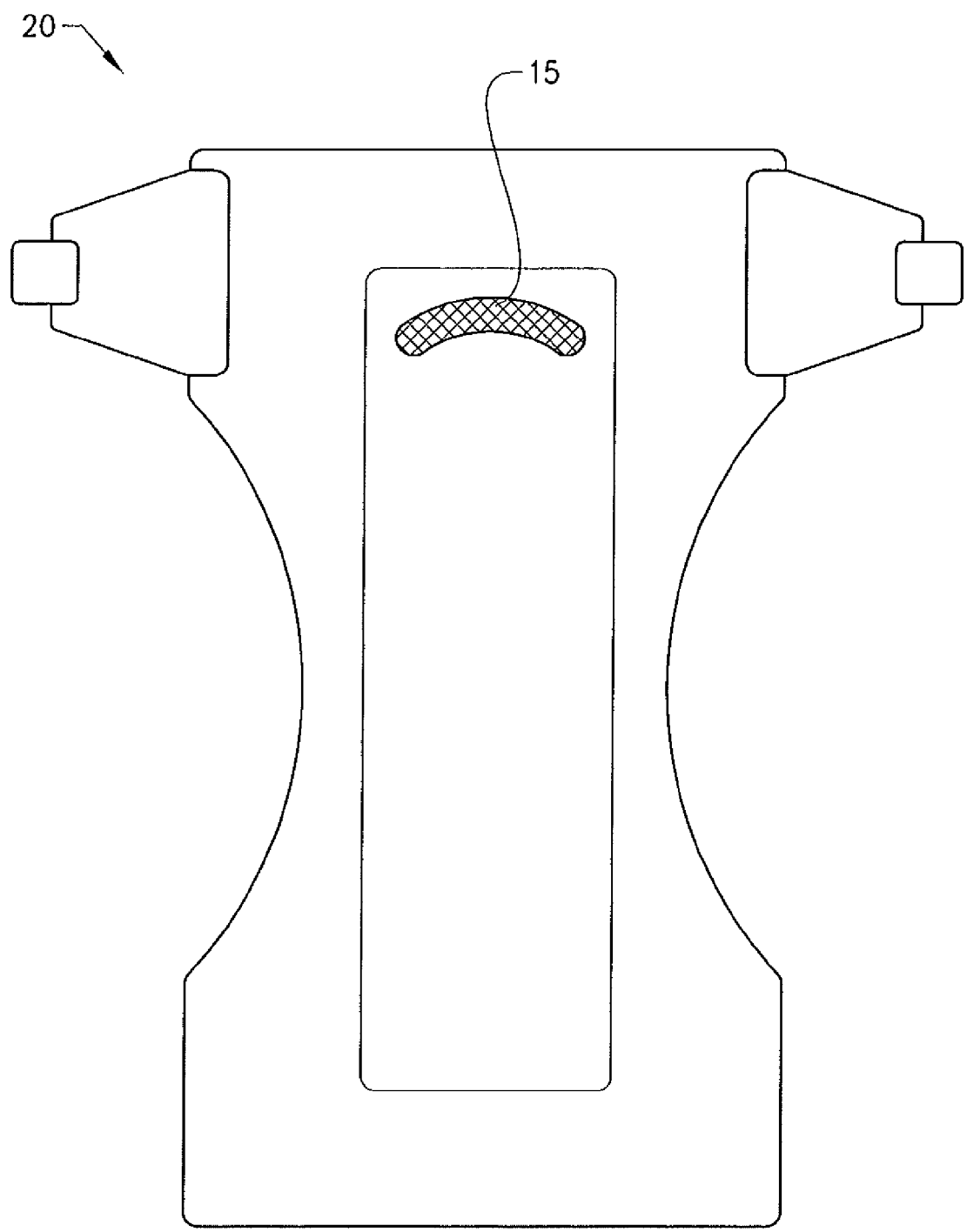
FIG. 4 is a top view of another diaper having three-dimensional structural elements applied to the top sheet.

FIGS. 3-4 illustrate three-dimensional structural elements of expanded ink applied to the top sheet of a diaper. The diaper 10 of FIG. 3, comprises a cluster of dots 11 applied to the top sheet at the rear end 12 of the wetting area 13 of the diaper. The three-dimensional structural elements will in this case act as distances between the wearers' skin and the surface of the diaper, and will also contribute to masking of the contents absorbed by the diaper. Liquid barriers 14 are applied in the crotch region of the diaper, and are formed of continuous lines of expanded ink. The diaper 20 of FIG. 4 has an alternative distance or barrier element 15 applied at the rear end, being in the form of a curved continuous line.

The invention claimed is:

1. A method of applying structural elements to an absorbent article having a longitudinal direction and a transverse direction, side edges extending in the longitudinal direction and end edges extending in the transverse direction, said absorbent article comprising a top sheet and a back sheet, the method comprising:
    applying expandable ink to the top sheet at at least a central area of the top sheet, and
    activating the expandable ink to obtain three-dimensional structural elements on the top sheet, such that a height of the three-dimensional structural elements at the central area decreases in a direction from the center of the central area toward the side edges.

2. The method of claim 1, wherein the expandable ink is applied on 1-50% of the surface area of the top sheet.

3. The method of claim 1, wherein the expandable ink is activated by subjecting the top sheet to heat.

4. The method of claim 3, wherein the heat is generated from one of infra-red radiation, hot air, microwaves, and a heated embossing roll.

5. The method of claim 1, wherein the expandable ink is activated by UV radiation.

6. The method of claim 1, wherein the expandable ink comprises a polymer, a solvent and a blowing agent or expandable microspheres.

7. The method of claim 1, wherein the expandable ink is applied as one or more liquid barriers selected from: in a crotch region along at least a part of the longitudinal side edges; a transverse front of the absorbent article; and a back region of the absorbent article.

8. The method of claim 7, wherein the one or more liquid barriers are formed of continuous and/or dotted lines.

9. The method of claim 1, wherein a cluster of dots of expandable ink is applied in a central longitudinal part of the absorbent article, forming a raised portion, and wherein a ratio between a height of the dots and a distance between the dots in the cluster is at least 1:1.

10. The method of claim 1, wherein the expandable ink is applied along at least a part of a transverse end edge of the absorbent article.

11. The method of claim 1, wherein a hydrophobic ink is applied along at least a part of at least one of a longitudinal side edge and a transverse end edge, and a hydrophilic ink is applied in a central and longitudinal part of the top sheet.

12. The method of claim 1, wherein the top sheet has a first surface facing away from the back sheet, and a second surface facing towards the back sheet, and wherein the expandable ink is applied to one or both of said first and second surfaces.

13. The method of claim 1, wherein the structural elements are applied on an absorbent article that is one of: a sanitary napkin; a panty liner; a male or female incontinence article; and a diaper.

14. An absorbent article comprising a top sheet provided with three-dimensional structural elements, wherein the three-dimensional structural elements consist of expandable ink that has been applied to the top sheet at at least a central area of the top sheet, and that has been subsequently activated at least partly to form the three-dimensional structural elements, such that a height of the three-dimensional structural elements at the central area decreases in a direction from the center of the central area toward side edges of the absorbent article.

15. The absorbent article of claim 14, wherein the three-dimensional structural elements have a height of 0.1-15 mm.

16. The absorbent article of claim 14, wherein 1-50% of the top sheet is covered with expandable ink.

17. A method of applying structural elements to an absorbent article having a longitudinal direction and a transverse direction, side edges extending in the longitudinal direction and end edges extending in the transverse direction, said absorbent article comprising a top sheet and a back sheet, the method comprising:
   applying expandable ink to the top sheet, at least some of the expandable ink being hydrophilic, and
   activating the expandable ink to obtain three-dimensional structural elements on the top sheet, wherein a cluster of dots of expandable ink is applied in a central longitudinal part of the absorbent article, forming a raised portion, and wherein a ratio between a height of the dots and a distance between the dots in the cluster is at least 1:1.

* * * * *